United States Patent [19]
Sredni et al.

[11] Patent Number: 5,475,030
[45] Date of Patent: * Dec. 12, 1995

[54] COMPLEXES OF TELLURIUM AND SELENIUM DERIVATIVES

[75] Inventors: Benjamin Sredni, Yona Hanavi Street 22, Beni Brak, Israel; Leo Pavliv, Somerville, N.J.; Michael Albeck, 8 Harel Street, Ramat-Gan, Israel, 52223

[73] Assignees: Michael Albeck; Benjamin Sredni, both of Israel

[*] Notice: The portion of the term of this patent subsequent to May 29, 2007, has been disclaimed.

[21] Appl. No.: 123,422

[22] Filed: Sep. 17, 1993

Related U.S. Application Data

[60] Continuation of Ser. No. 500,296, Mar. 27, 1990, abandoned, which is a division of Ser. No. 172,643, Mar. 24, 1988, Pat. No. 4,929,739.

[51] Int. Cl.$^6$ ............................................. A61K 31/185
[52] U.S. Cl. ................................... 514/553; 514/578
[58] Field of Search .............................. 514/578, 553

[56] References Cited

U.S. PATENT DOCUMENTS 4,929,739   5/1990   Srendi et al. .................... 549/347

*Primary Examiner*—C. Warren Ivy
*Assistant Examiner*—Amelia Owens
*Attorney, Agent, or Firm*—Hedman, Gibson & Costigan

[57] ABSTRACT

A novel complex of a class of tellurium and selenium compounds is disclosed, which is based on a complexing agent and the particular compound to be complexed.

12 Claims, No Drawings

COMPLEXES OF TELLURIUM AND SELENIUM DERIVATIVES

This is a continuation of application Ser. No. 07/500,296, filed Mar. 27, 1990; now abandoned which is a Divisional of application Ser. No. 07/172,643, filed Mar. 24, 1988, U.S. Pat. No. 4,929,739.

BACKGROUND OF THE INVENTION

In U.S. Pat. No. 4,761,490, which is incorporated herein by reference, there are described certain organic compounds of tellurium and selenium which are active in vitro and in vivo for the production of cytokines. These compounds are also useful for a number of diseases as set forth in Ser. No. 782,129. One phenomenon of these compounds of tellurium and selenium is the relatively insoluble nature of the compounds in aqueous media which causes difficulty in the preparation of pharmaceutical compositions for parental administration. It has been found by the applicants that certain polycarboxylic acids will form a stable complex with certain organic compounds of tellurium and selenium.

Accordingly, it is a primary object of this invention to provide novel complexes of certain organic compounds of tellurium and selenium with non-toxic complexing agents which have increased water solubility.

It is also an object of this invention to provide a novel pharmaceutical composition which is based on the use of a novel complex of certain compounds of tellurium and selenium with non-toxic complexing agents.

It is also a further object of this invention to provide novel methods for the induction of cytokines using complexes of certain organic compounds of tellurium and selenium with non-toxic complexing agents.

SUMMARY OF THE INVENTION

The present invention provides a complex of a compound of the following formula:

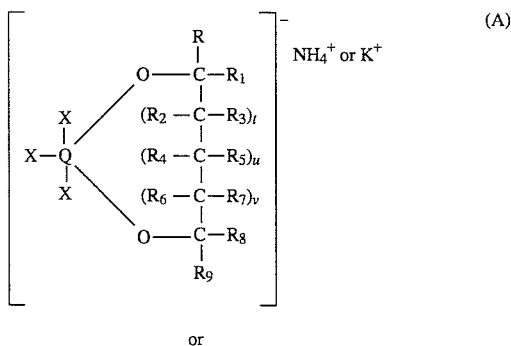

(A)

or

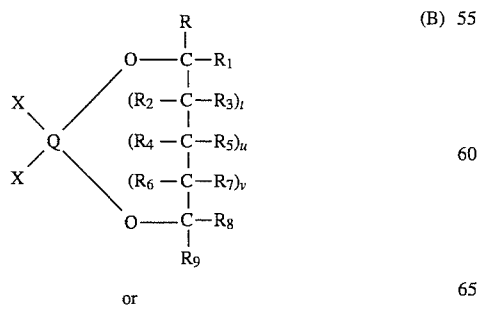

(B)

or $TeO_2$ (C)

or $PhTeCl_3$ (D)

or $(C_6H_5)_4^+P$  $(TeCl_3(O_2C_2H_4)^-$ (E)

wherein Q is Te or Se; t is 1 or 0; u is 1 or 0; v is 1 or 0; R, $R_1$, $R_2$, $R_3$, $R_4$, $R_5$, $R_6$, $R_7$, $R_8$ and $R_9$ are the same or different and are independently selected from the group consisting of hydrogen, hydroxyalkyl of 1 to 5 carbons, hydroxy, alkyl of from 1 to 5 carbon atoms, halogen, haloalkyl of 1 to 5 carbon atoms, carboxy, alkylcarbonylalkyl of 2 to 10 carbons, alkanoyloxy of 1 to 5 carbon atoms, carboxyalkyl of 1 to 5 carbon atoms, acyl, amido, cyano, amidoalkyl of 1 to 5 carbons, N-monoalkylamidoalkyl of 2 to 10 carbons, N,N-dialkylamidoalkyl of 4 to 10 carbons, cyanoalkyl of 1 to 5 carbons, alkoxy of 1 to 5 carbon atoms, alkoxyalkyl of 2 to 10 carbon atoms and —$COR_{10}$ wherein $R_{10}$ is alkyl of from 1 to 5 carbons; and X is halogen; while the potassium and ammonium salts may be used, it is understood that other pharmaceutically acceptable salts are within the scope of the invention, The compounds with the five membered rings are preferred.

As used herein and in the appended claims, the term alkyl of 1 to 5 carbon atoms includes straight and branched chain alkyl groups such as methyl; ethyl; n-propyl; n-butyl, and the like; the term hydroxyalkyl of 1 to 5 carbon atoms includes hydroxymethyl; hydroxyethyl; hydroxy-n-butyl; the term haloalkyl of 1 to 5 carbon atoms includes chloromethyl; 2-iodoethyl; 4-bromo-n-butyl; iodoethyl; 4-bromo-n-pentyl and the like; the term alkanoyloxy of 1 to 5 carbon atoms includes acetyl, propionyl, butanoyl and the like; the term carboxyalkyl includes carboxymethyl, carboxyethyl, ethylenecarboxy and the like; the term alkylcarbonylalkyl includes methanoylmethyl, ethanoylethyl and the like; the term amidoalkyl includes —$C_2CONH_2$; —$CH_2CH_2CONH_2$; —$CH_2CH_2CH_2CONH_2$ and the like; the term cyanoalkyl includes —$CH_2CN$; —$CH_2CH_2CN$; —$CH_2CH_2CH_2CN$ and the like; the term alkoxy of 1 to 5 carbon atoms includes methoxy, ethoxy, n-propoxy, n-pentoxy and the like; the terms halo and halogen are used to signify chloro, bromo, iodo and fluoro; the term acyl includes $R_{16}CO$ wherein $R_{16}$ is H, or alkyl of 1 to 5 carbons such as methanoyl, ethanoyl and the like; the term aryl includes phenyl, alkylphenyl and naphthyl; the term N-monoalkylamidoalkyl includes —$CH_2CH_2CONHCH_3$, —$CH_2CONHCH_2CH_3$; the term N,N-dialkylamidoalkyl includes —$CH_2CON(CH_3)_2$; $CH_2CH_2CON(CH_2CH_3)$. Compounds which are based on tellurium are the presently preferred compounds of the invention. The tellurium based compounds that are preferred include those of the formula:

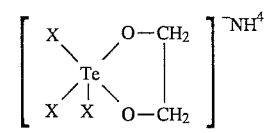

wherein X is halogen. The preferred halogen species is chloro. These compounds are capable of inducing IL-2 formation as well as the proliferation of IL-2 producer cells and the activation of IL-2 receptor sites.

Useful dihydroxy compounds for use in the preparation of compounds of structure A or B, include those of formula I wherein R, $R_1$, $R_4$ and $R_5$ are as shown in the Table:

TABLE $$\begin{array}{c} R \quad R_4 \\ | \quad | \\ HO-C-C-OH \\ | \quad | \\ R_1 \quad R_5 \end{array} \quad (I)$$

| R | $R_1$ | $R_4$ | $R_5$ |
|---|---|---|---|
| H | H | H | H |
| H | Cl | H | H |
| H | $OCH_3$ | H | H |
| H | $COOCH_3$ | H | H |
| H | H | CN | H |
| H | CHO | H | H |
| H | H | COOH | H |
| H | $CH_2COOH$ | H | H |
| H | H | $CHCOOCH_3$ | H |
| H | I | H | H |
| H | H | Br | H |
| H | H | $CONH_2$ | H |
| H | H | $CH_2OH$ | H |
| H | COOH | H | H |

Other dihydroxy compounds for use in the preparation of compounds A and B include those of formula II wherein R, $R_1$, $R_2$, $R_3$, $R_4$ and $R_5$ are as shown in the Table:

$$\begin{array}{c} R \quad R_2 \quad R_4 \\ | \quad | \quad | \\ HO-C-C-C-OH \\ | \quad | \quad | \\ R_1 \quad R_3 \quad R_5 \end{array} \quad (II)$$

| R | $R_1$ | $R_2$ | $R_3$ | $R_4$ | $R_5$ |
|---|---|---|---|---|---|
| H | H | H | H | H | H |
| H | H | Cl | H | H | H |
| H | $CH_2OH$ | H | H | H | H |
| H | H | OH | H | H | H |
| H | H | H | $CH_3$ | H | H |
| H | H | H | $CH_2Cl$ | H | H |
| H | H | H | COOH | H | H |
| H | H | H | $CH_2COOH$ | H | H |
| H | H | H | CHO | H | H |
| H | H | H | H | H | $CH_2CHO$ |
| H | H | $CONH_2$ | H | H | $CH_3$ |
| H | H | H | CN | H | H |
| H | H | H | H | $CH_2CONH_2$ | H |
| H | H | H | $COOCH_3$ | H | H |
| H | H | $OCH_3$ | H | H | H |

Other dihydroxy compounds for use in making compound of formula A and B include those of formula III wherein R, $R_1$, $R_2$, $R_3$, $R_4$ and $R_5$ are as shown in the Table.

$$\begin{array}{c} R \quad R_2 \quad R_4 \quad R_8 \\ | \quad | \quad | \quad | \\ HO-C-C-C-C-OH \\ | \quad | \quad | \quad | \\ R_1 \quad R_3 \quad R_5 \quad R_9 \end{array} \quad (III)$$

| R | $R_1$ | $R_2$ | $R_3$ | $R_4$ | $R_5$ | $R_8$ | $R_9$ |
|---|---|---|---|---|---|---|---|
| H | H | H | H | H | H | H | H |
| H | H | Cl | H | H | H | H | H |
| H | H | H | H | Br | H | H | H |
| H | H | $OCH_3$ | H | H | H | H | H |
| H | H | $CONH_2$ | H | H | H | H | H |
| H | Br | H | H | Br | H | H | H |
| H | H | H | H | $CH_2COOH$ | H | H | H |
| H | H | Cl | Cl | H | H | H | H |
| H | $CH_2COOH$ | H | H | H | H | H | H |
| H | H | $CH_3$ | H | H | H | H | H |
| H | $CH_3$ | H | H | H | H | H | H |
| H | $CH_2Cl$ | H | H | H | H | H | H |
| H | H | H | I | H | H | H | H |
| H | $CH_2CN$ | H | H | H | H | H | H |
| H | H | H | H | $CH_2CH_2OH$ | H | H | H |

Additional dihydroxy compounds include those of formula IV wherein R, $R_1$, $R_2$, $R_3$, $R_4$ and $R_5$ are as shown in the Table.

$$\begin{array}{c} R \quad R_2 \quad R_4 \quad R_6 \quad R_8 \\ | \quad | \quad | \quad | \quad | \\ HO-C-C-C-C-C-OH \\ | \quad | \quad | \quad | \quad | \\ R_1 \quad R_3 \quad R_5 \quad R_7 \quad R_9 \end{array} \quad (IV)$$

| R | $R_2$ | $R_2$ | $R_3$ | $R_4$ | $R_5$ | $R_6$ | $R_7$ | $R_8$ | $R_9$ |
|---|---|---|---|---|---|---|---|---|---|
| H | H | H | H | H | H | H | H | H | H |
| H | H | Cl | H | H | H | Cl | H | H | H |
| H | H | Cl | Cl | H | H | H | H | H | H |
| H | H | $CONCH_3$ | H | H | H | Br | H | H | H |
| H | H | Br | H | H | H | $CON(CH_3)_2$ | H | H | H |
| H | H | H | $OCH_3$ | H | H | H | H | H | H |
| H | H | H | H | $OCH_3$ | H | H | H | H | H |
| H | H | H | H | $CH_2COOH$ | H | H | H | H | H |
| H | H | COOH | H | H | H | H | H | H | H |
| H | $CH_3$ | H | H | H | H | H | H | H | H |
| $CH_3$ | H | H | H | H | $CH_3$ | H | H | H | H |

-continued $$HO-\underset{R_1}{\overset{R}{C}}-\underset{R_3}{\overset{R_2}{C}}-\underset{R_5}{\overset{R_4}{C}}-\underset{R_7}{\overset{R_6}{C}}-\underset{R_9}{\overset{R_8}{C}}-OH \qquad (IV)$$

| R | $R_2$ | $R_2$ | $R_3$ | $R_4$ | $R_5$ | $R_6$ | $R_7$ | $R_8$ | $R_9$ |
|---|---|---|---|---|---|---|---|---|---|
| H | $CH_2CH_3$ | H | H | H | H | H | Cl | H | H |
| H | $CH_2CN$ | H | H | $CH_2OH$ | H | H | H | H | H |
| H | H | H | I | H | H | H | H | CN | H |
| H | $CH_2CH_2COOH$ | H | H | H | H | H | H | H | H |
| H | H | CHO | H | H | H | H | H | H | H |
| H | H | H | F | H | H | H | H | H | H |

DETAILED DESCRIPTION OF THE INVENTION

The complexes of the invention may be formed by contacting a compound of Formulas A–E with a non-toxic pharmaceutically acceptable complexing agent which forms a water soluble complex with said tellurium or selenium compound. Suitable complexing agents include hydroxy polycarboxylic acids, polycarboxylic acids or polyhydroxy polycarboxylic acids. Generally, it is preferred to prepare the complexes of the invention by contacting a compound of Formulas A–E with a buffer system containing either citric acid or tartaric acid and a corresponding alkali metal salt thereof, such as sodium or potassium.

Generally equimolar amounts of acids and the corresponding alkali metal salts may be combined in aqueous solutions with a compound of Formulas A–E to form the complex of the invention; 0.05M–0.5M concentrations of the buffer are preferred but higher or lower amounts may be utilized provided that the concentration is adequate to dissolve the particular compound of Formulas A–E. Higher molarities may be used to provide concentrates that may be diluted prior to 1V administration or to prepare other dosage forms. The amount of the compound of Formulas A–E is dependent on the ultimate use of the product. It has been found that in the case of the citrate, concentrations of 5mg/ml and greater of ammonium trichloro (dioxoethylene-0,0') tellurate may be solubilized according to the present invention. This is in contrast to the phosphate buffer (PBS) from which only about 200 mcg/ml of ammonium trichloro (dioxoethylene-0,0') tellurate can be solubilized. It is preferred to employ the aqueous solution of the complex directly without recovering and redissolving the complex. The complex is stable when frozen, or at refrigerated, room or elevated temperatures. The compounds of the invention may be administered to mammals for treatment of cancer, immune deficiencies, autoimmune diseases and infectious diseases using amounts that are effective in each condition. The treatment will alleviate the symptoms of these diseases by causing the mammalian body to produce increased amounts of lymphokines. The invention also includes the in vitro production of increased amounts of cytokines such as lymphokines and or their receptors and the use of these materials as therapeutic agents to be administered to mammals for the alleviation of cancer, immune deficiencies and infectious diseases. It is contemplated that the composition of the invention may be used in combination with other anti-cancer chemotherapeutic agents such as cyclophosphamide.

The term cancer is used to include leukemia and solid tumors that arise spontaneously, by contact with a carcinogenic agent, by irradiation or by onco-viruses. These conditions are well known to those who are skilled in the art and include such conditions as adrenal tumors, bone tumors, gastrointestinal tumors, brain tumors, breast tumors, skin tumors, lung tumors, ovarian tumors, genitourinary tumors and the like. The Merck Manual 13th Edition, Merck & Co. (1977) describes many of these conditions. Pages 647–650; 828–831; 917–920; 966; 970–974; 1273, 1277; 1371–1376; 1436–1441; 1563; 1612–1615 of the publication are incorporated herein by reference.

The term immunodeficiency diseases is used to describe a diverse group of conditions such as Acquired Immunedeficiency Syndrome (AIDS) characterized chiefly by an increased susceptibility to various infections with consequent severe acute, recurrent and chronic disease which result from one or more defects in the specific or nonspecific immune systems. Pages 205–220 of the Merck Manual 13th Edition describe many of these conditions and they are incorporated herein by reference.

The term auto immune diseases includes disorders in which the immune system produces autoantibodies to an endogenous antigen, with consequent injury to tissues. Pages 241–243 of the Merck Manual 13th Edition describe these conditions and they are incorporated herein by reference.

The term infectious diseases includes those pathologic conditions that arise from bacterial, viral or fungus organisms that invade and disrupt the normal function of the mammalian body. Pages 3–149 of the Merck Manual 13th Edition describe these conditions and they are incorporated herein by reference.

The compounds may be administered orally, parenterally, transcutaneously, topically or by contacting mucous membranes. The compounds may be administered orally in hard or soft gel liquid capsules, in solutions or suspension capsules or tablets that may be prepared using conventional excipients, binders, disintegrating agents and the like. The parenteral route may be intramuscular, intravenous, intradermal using a sustained release carrier or subcutaneous. The concentration of the compounds in combination with a pharmaceutical carrier is not critical and is a matter of choice. Remington's Practice of Pharmacy, 9th, 15th or 16th Ed. describes various pharmaceutical carriers and is incorporated herein by reference.

It has been found that a number of the tellurium compounds useful in the practice of the invention will hydrolyze in the presence of water. These hydrolyzed compositions are active in vivo and in vitro although the hydrolyzed compositions eventually decompose and lose their ability to induce lymphokine secretion. For this reason, the compositions should be freshly prepared. If the compounds are administered orally in dry form, they are active in inducing the production of lymphokines. Preferably, the compounds should be kept under anhydrous conditions until just prior to being used.

It has been found that certain compounds such as $TeO_2$ alone will induce lymphokine production in producer T-cell lymphocytes in vitro and in vivo but it will not cause proliferation of lymphokines in producing cells such as IL-2 producer cells or activate the receptor site in responder T-cell lymphocytes. Thus the invention also contemplates the use alone of $TeO_2$ and tellurium compounds that are active as lymphokine inducers.

Topical compositions may be prepared by dispersing the compounds in a hydrophillic or hydrophobic cosmetic base. Topical compositions include liquids, ointments, creams, lotions, gels, and pastes. Petroleum jelly or commercial preparations such as Oil of Olay may be used. The concentration may be from 0.0001–10% on a weight/weight basis.

The dosage of the compounds of the invention used to stimulate lymphokine production or treat the specific disease condition described wherein may be varied depending on the particular disease and the stage of the disease. Generally an amount of the compound may be administered which will range from $0.05 \times 10^{-3}$ to $1 \times 10^{-3}$ g/Kg of body weight and preferably from $0.1 \times 10^{-3}$ to $0.5 \times 10^{-3}$ g/Kg of body weight. For example a dosage of 1–3 mg per day for a 75 Kg mammal is contemplated as a sufficient amount to induce lymphokine production but the dosage may be adjusted according to the individual response and the particular condition that is being treated. For the treatment of AIDS 1.0–9.0 $mg/m^2$ may be given IV three times a week. In addition, the compound of the invention may be administered concomitantly with agents such as 9-(1,3-dihydroxy-2-propoxymethyl) guanine (DHPG); and/or AZT.

In addition to treating the mammalian disorders described hereinabove, the compounds may be utilized for veterinary purposes in the treatment of viral and immune diseases that afflict horses, ungulates and fowl. These disorders may be treated using quantities of the compound that may be used in treating the mammalian disorders described hereinabove.

For in vitro use, cells may be stimulated to produce lymphokines by use of $1 \times 10^{-8}$ to $1 \times 10^{-4}$, preferably $1 \times 10^{-7}$ to $1 \times 10^{-5}$ g of compound per $10^6$ cells/mi.

Preliminary toxicity studies in mice have established an $LD_{50}$ of 300 µg./25 g of body weight in 6 week old mice for the compound of Example 1. The compounds may be used as anti-bacterial or anti-viral agents in plants or in animals. Virus infections such as West Nile virus infections in mice are susceptible to the compound of the Example 1 at a dose of 10 µg/day/mouse. Plant bacterial infections such as crown gall caused by *Agrobacterium tumefaciens* may be treated or prevented by the application of a 0.1% solution of compounds of the invention.

EXAMPLE 1

Two citrate buffer solutions are prepared by combining aqueous 0.05M sodium citrate with 0.05M citric acid or 0.1M sodium citrate. and 0.1M citric acid. The pH is about 4 depending on the amount of Compound A added. To these solutions are added up to 5 mg/ml of ammonium trichloro (dioxoethylene-0,0') tellurate.

After storage at various temperatures for about two and a half months, dilutions of these solutions were prepared and a mouse spleen assay was performed as follows:

Spleens were removed from male Balb-c mice 6 to 8 weeks of age. The spleen cells were pushed through stainless steel 60 mesh (U.S. standard) nets resting in 5 mm Petri dishes containing PBS in order to separate the cells. The cells were then collected into centrifuge tubes and spun at 1000 rpm for 10 minutes. The supernatant was discarded and cells were treated with 5 ml of hypotonic buffer (0.15 $MNH_4Cl$; 0.01M $KHCO_3$ dissolved in double distilled water, pH 7.2 ) for exactly two minutes. Thereafter, PBS* was added to the cells and the test tubes were centrifuged for 10 minutes at 1000 rpm. The cells were rinsed twice and counted in a heamocytometer using trypan blue to test for viability. The cells were brought to a concentration of $10^7$ viable cells/mi. The cells were contacted with 25 mg/ml of

| *NaCl | 8.0 g |
|---|---|
| KCl | 200 mg |
| $Na_2HPO_4$ | 1150 mg |
| $KH_2PO_4$ | 200 mg |
| $CaCl_2$ (anhyl) | 100 mg/L |
| $MgCl_2 6H_2O$ | 100 mg/L |
| $H_2O$ | sufficient to make 1 liter |

PMA and with varying amounts of the complex in water. Thereafter, the cells were incubated at 37° C., 7.5% CO for 96 h. Supernatants were collected and assayed for IL-2 activity using tritiated thymidine ($^3$H-TdR). The results for the assay of 25% and 12.5% supernatants are shown as counts per million (cpm) in a beta scintillator and are set forth in Table I. Table I shows the induction of IL-2 activity that is obtained with varying amounts of the complex.

TABLE 1

| | ammonium trichloro (dioxoethylene-0,0) tellurate | % supernatant | |
|---|---|---|---|
| | µg/ml | 25% | 12.5% |
| 0.05M Citrate | 0.5 | 76138 | 99850 |
| | 0.1 | 91022 | 65518 |
| | 0.05 | 5450 | 1728 |
| 0.1 citrate | 0.5 | 65632 | 50778 |
| | 0.1 | 55127 | 27582 |
| | 0.05 | 3432 | 1597 |
| control with PBS $Mg^+ Ca^+$ placebo | 0.5 | 43833 | 35270 |
| | 0.1 | 44378 | 28035 |
| | 0.05 | 3762 | 1865 |
| 1:10 | 0 | 5157 | 2878 |
| 1:40 | 0 | 4085 | 4172 |
| 1:100 | 0 | 3320 | 2192 |

These tests show that the citrate complex is as effective as the uncomplexed control.

EXAMPLE 2

Using the same procedures that are employed in Example 1, 0.02M tartrate buffer is prepared from 0.02M tartaric acid and 0.02M potassium tartrate in a 1:4 ratio. A 0.04M tartrate buffer in also prepared using the same procedures. The complex is formed by adding ammonium trichloro (dioxoethylene-0,0'-) tellurate to the aqueous tartrate buffer. The effectiveness of the complex in stimulating IL-2 production was determined in the mouse spleen assay. The results are shown in Table II:

TABLE 2

| ammonium trichloro (deoxyethylene-0,0'-) tellurate μg/ml | | supernatant (cpm) | |
|---|---|---|---|
| | | 25% | 12.5% |
| 0.02M | 0.5 | 64563 | 58015 |
| tartrate | 0.1 | 11258 | 5722 |
| buffer | 0.05 | 1152 | 887 |
| 0.04M | 0.5 | 1513 | 610 |
| tartrate | 0.1 | 2610 | 1598 |
| buffer | 0.05 | 1423 | 665 |
| control | 0.5 | 43833 | 35270 |
| with PBS | 0.1 | 44378 | 28035 |
| $Mg^{++}$ & $Ca^{++}$ | 0.05 | 3762 | 1865 |

EXAMPLE 3

Citrate and tartrate complexes of ammonium trichloro (dioxoethylene-0,0') tellurate are tested for the stimulation of human mononuclear cells.

Venous whole blood (with heparin; Evans 10 IU/ml blood) is diluted with RPMI in a ratio of 1:1. The diluted blood is gently placed on Lymphoprep (Nylgard & Co., Oslo, Norway, density 1.077 g/ml) two parts of diluted blood on one part of Lymphoprep. Each tube is provided with 3 ml Lymphoprep and 6 to 7 ml diluted blood. The tubes are centrifuged 30 minutes at 1600 rpm at room temperature. After the centrifugation mononuclear cells are collected from the interphase fraction and washed with RPMI three times. The cells are resuspended in RPMI, counted on a hemocytometer, using trypan blue to test for viability and then are brought to a concentration of $1 \times 10^{-6}$ cells per ml in enriched RPMI. The concentrations set forth in Table 3 were added in a volume of 10% of cell mixture. Aliquots of 0.2 ml from each sample were placed in wells of microplates (NUNC) (triplicates). The microplates are incubated for 72 hours at 37° C. after which $^3$H-methylthymidine, 1U Ci/well (Nuclear Research Center, Israel) are added to the cultures. Cells were further incubated overnight and harvested with a cell harvester. Proliferation was measured with a beta scintillation counter and the results are set forth in Table 3:

TABLE 3

| ammonium trichloro (deoxyethylene-0,0'-) tellurate μg/ml | | PMA | |
|---|---|---|---|
| | | 1.5 ng/ml cells | 0.5 ng/ml cells |
| 0.02M | 0.5 | 1418 | 1680 |
| tartrate | 0.1 | 30992 | 20620 |
| buffer | 0.05 | 22883 | 12800 |
| 0.04 | 0.5 | 2762 | 527 |
| tartrate | 0.1 | 20713 | 12990 |
| buffer | 0.005 | 15327 | 16782 |
| 0.05 | 0.5 | 1822 | 745 |
| citrate | 0.1 | 49402 | 8713 |
| | 0.05 | 3937 | 5298 |
| control | 0.5 | 3287 | 2945 |
| PBS | 0.1 | 42857 | 19810 |
| $Mg^+$ & $Ca^{++}$ | 0.05 | 12923 | 6663 |

We claim:

1. A complex of a compound of the formula:

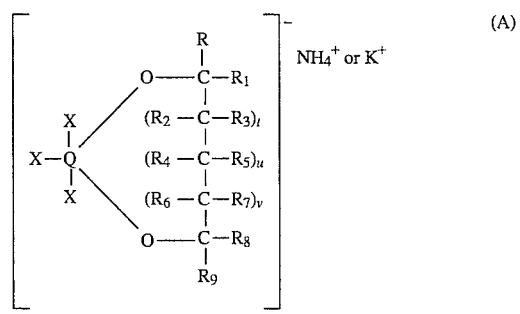

or

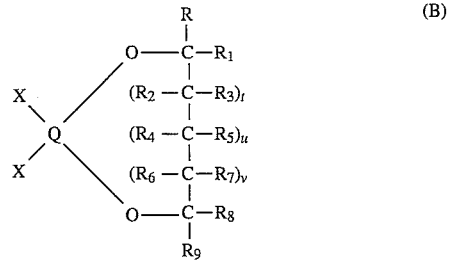

or

or

or

wherein Q is Te or Se; t is 1 or 0; u is 1 or 0; v is 1 or 0; R, $R_1$, $R_2$, $R_3$, $R_4$, $R_5$, $R_6$, $R_7$, $R_8$ and $R_9$ are the same or different and are independently selected from the group consisting of hydrogen, hydroxyalkyl of 1 to 5 carbons, hydroxy, alkyl of from 1 to 5 carbon atoms, halogen, haloalkyl of 1 to 5 carbon atoms, carboxy, alkylcarbonylalkyl of 2 to 10 carbons, alkanoyloxy of 1 to 5 carbon atoms, carboxyalkyl of 1 to 5 carbon atoms, acyl, amido, cyano, amidoalkyl of 1 to 5 carbons, N-monoalkylamidoalkyl of 2 to 10 carbons, N,N-dialkylamidoalkyl of 4 to 10 carbons, cyanoalkyl of 1 to 5 carbon atoms, alkoxy of 1 to 5 carbon atoms, alkoxyalkyl of 2 to 10 carbon atoms and —$COR_{10}$ wherein $R_{10}$ is alkyl of from 1 to 5 carbons; and X is halogen with a non-toxic pharmaceutically acceptable complexing agent.

2. A complex as defined in claim 1, wherein the complexing agent is selected from the group consisting of hydroxy polycarboxylic acids, polycarboxylic acids or polyhydroxy polycarboxylic acids.

3. A complex as defined in claim 2, wherein the complexing agent is a hydroxy polycarboxylic acid.

4. A complex as defined in claim 2, wherein the complexing agent is a polycarboxylic acid.

5. A complex as defined in claim 2, wherein the complexing agent is a polyhydroxy polycarboxylic acid.

6. A complex as defined in claim 2, wherein the compound is of the formula:

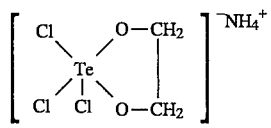

7. A complex as defined in claim 6, wherein the complex contains the citrate ion.

8. A complex as defined in claim 6, wherein the complex contains the tartrate ion.

9. A pharmaceutical composition which comprises the complex of claim 1 and a pharmaceutical carrier.

10. A pharmaceutical composition which comprises the complex of claim 7 and a pharmaceutical carrier.

11. A pharmaceutical composition which comprises the complex of claim 8 and a pharmaceutical carrier.

12. A pharmaceutical composition which comprises the complex of claim 4 and a pharmaceutical carrier.

* * * * *